US009878027B2

(12) United States Patent
Jordan et al.

(10) Patent No.: US 9,878,027 B2
(45) Date of Patent: Jan. 30, 2018

(54) IMMUNOGENIC COMPOSITION COMPRISING MYCOPLASMA ANTIGENS

(71) Applicants: Dianna M. Murphy Jordan, Ames, IA (US); Brian Thomas Martinson, Duncombe, IA (US); Christine Margaret Muehlenthaler, Ames, IA (US); Axel Neubauer, St. Joseph, MO (US); Arun V. Iyer, Ames, IA (US)

(72) Inventors: Dianna M. Murphy Jordan, Ames, IA (US); Brian Thomas Martinson, Duncombe, IA (US); Christine Margaret Muehlenthaler, Ames, IA (US); Axel Neubauer, St. Joseph, MO (US); Arun V. Iyer, Ames, IA (US)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/135,791

(22) Filed: Dec. 20, 2013

(65) Prior Publication Data
US 2014/0186393 A1  Jul. 3, 2014

Related U.S. Application Data

(60) Provisional application No. 61/747,026, filed on Dec. 28, 2012.

(51) Int. Cl.
*A61K 39/00* (2006.01)
*A61K 39/02* (2006.01)
*A61K 35/22* (2015.01)

(52) U.S. Cl.
CPC .......... *A61K 39/0241* (2013.01); *A61K 35/22* (2013.01); *A61K 2039/70* (2013.01)

(58) Field of Classification Search
None
See application file for complete search history.

(56) References Cited

U.S. PATENT DOCUMENTS

| | | | | |
|---|---|---|---|---|
| 7,018,638 | B2 * | 3/2006 | Chu et al. | 424/201.1 |
| 7,169,394 | B2 * | 1/2007 | Chu et al. | 424/201.1 |
| 7,381,414 | B2 * | 6/2008 | Lin et al. | 424/264.1 |
| 7,622,124 | B2 * | 11/2009 | Chu et al. | 424/201.1 |
| 7,666,439 | B2 * | 2/2010 | Chu et al. | 424/264.1 |
| 7,959,927 | B2 * | 6/2011 | Chu et al. | 424/201.1 |
| 8,187,588 | B2 * | 5/2012 | Chu et al. | 424/93.4 |
| 8,444,989 | B1 * | 5/2013 | Ohnesorge et al. | 424/164.1 |
| 8,852,613 | B2 * | 10/2014 | Ohnesorge et al. | 424/264.1 |
| 9,273,281 | B2 * | 3/2016 | Jordan | A61K 39/0241 424/248.1 |
| 9,650,600 | B2 * | 5/2017 | Galvin | C07K 14/30 |
| 9,650,601 | B2 * | 5/2017 | Nitzel | A61K 39/295 |
| 9,662,385 | B2 * | 5/2017 | Dominowski | A61K 39/39 |
| 2003/0064079 | A1 * | 4/2003 | Goudie et al. | 424/248.1 |
| 2003/0109473 | A1 * | 6/2003 | Keich et al. | 514/44 |
| 2005/0013823 | A1 * | 1/2005 | Keich et al. | 424/184.1 |
| 2005/0037027 | A1 * | 2/2005 | Lin et al. | 424/248.1 |
| 2008/0185755 | A1 * | 8/2008 | Deaville et al. | 264/257 |
| 2012/0213816 | A1 * | 8/2012 | Chu et al. | 424/203.1 |
| 2013/0052717 | A1 * | 2/2013 | Liu | C12N 7/00 435/235.1 |
| 2013/0230558 | A1 * | 9/2013 | Ohnesorge et al. | 424/264.1 |
| 2013/0266601 | A1 * | 10/2013 | Galvin et al. | 424/186.1 |
| 2013/0266602 | A1 * | 10/2013 | Nitzel et al. | 424/186.1 |
| 2013/0266603 | A1 * | 10/2013 | Nitzel et al. | 424/186.1 |
| 2014/0186393 | A1 * | 7/2014 | Jordan | A61K 39/0241 424/203.1 |
| 2014/0186394 | A1 * | 7/2014 | Jordan | C12N 1/20 424/203.1 |
| 2014/0370058 | A1 * | 12/2014 | Ohnesorge et al. | 424/264.1 |
| 2016/0136254 | A1 * | 5/2016 | Jordan | C12N 5/0686 435/347 |

FOREIGN PATENT DOCUMENTS

| | | |
|---|---|---|
| CN | 102258776 A | 11/2011 |
| EP | 1260581 A1 | 11/2002 |
| EP | 1862537 A1 | 12/2007 |
| GB | 1074920 A | 7/1967 |

(Continued)

OTHER PUBLICATIONS

Abstract and Claims in English for CN102258776, 2011.
Gaush et al., "Characterization of an Established Line of Canine Kidney Cells (MDCK). *1 (31293)". Proceedings of the Society for Experimental Biology & Medicine, vol. 122, No. 3, Jul. 1966, pp. 931-935.
Kobisch et al., "Swine Mycoplasmoses". Review Scientifique Et technique De L'OFfice International Des Epizooties, vol. 15, No. 4, 1996, pp. 1569-1605.
Mochizuki, Masami, "Growth characteristics of canine pathogenic viruses in MDCK cells cultured in RPMI 1640 medium without animal protein". Vaccine, vol. 24, 2006, pp. 1744-1748.
Sobko et al., "Development of Scientific Techniques for the Prevention of Mycoplasma Infections in Swine". Archiv Fuer Experimentelle Veterinaermedizin, vol. 43, No. 5, Jan. 1989, pp. 645-655. (Abstract in English on p. 654).
Volokhov et al., "Biological Enrichment of Mycoplasma Agents by Cocultivation with Permissive Cell Cultures". Applied and Environmental Microbiology, vol. 74, No. 17, Sep. 2008, pp. 5383-5391.
Bhogal et al., "Production of mycoplasma-specific antisera in rabbits immunologically tolerized at birth to mycoplasma medium constituents". Journal of Immunological Methods, vol. 97, No. 2, 1987, pp. 191-199.

(Continued)

Primary Examiner — Nita M. Minnifield
(74) Attorney, Agent, or Firm — Marc Began; Wendy M. Gombert

(57) ABSTRACT

The present invention relates to an immunogenic composition comprising: a) one or more antigen of *M. hyorhinis* and one or more antigens of *M. hyosynoviae*; and b) a pharmaceutically acceptable carrier. Furthermore, the present invention relates to an immunogenic composition that comprises a) one or more *mycoplasma* antigens of *mycoplasma* bacteria selected from the group consisting of *M. hyorhinis*, *M. hyopneumoniae* and *M. hyosynoviae*; and b) one or more components of a eukaryotic cell system. Moreover, the present invention also provides an immunogenic composition obtained by a method comprising a) cultivation of a *mycoplasma* bacteria selected from the group consisting of *M. hyorhinis*, *M. hyopneumoniae* and *M. hyosynoviae* in a serum-reduced, eukaryotic cell system; b) obtaining an antigen of such *mycoplasma* bacteria; and c) addition of a pharmaceutically acceptable carrier.

29 Claims, No Drawings

(56) References Cited

FOREIGN PATENT DOCUMENTS

| | | | |
|---|---|---|---|
| GB | 1137306 | A | 12/1968 |
| WO | 1993016726 | A2 | 9/1993 |
| WO | WO 2002/049666 | A2 * | 6/2002 |
| WO | 2009058833 | A2 | 5/2009 |
| WO | 2009126356 | A2 | 10/2009 |
| WO | 2011075379 | A1 | 6/2011 |
| WO | 2013152081 | A1 | 10/2013 |
| WO | 2013152083 | A2 | 10/2013 |
| WO | 2014105672 | A1 | 7/2014 |
| WO | WO 2014/105671 | A1 * | 7/2014 |
| WO | WO 2014/105672 | A1 * | 7/2014 |

OTHER PUBLICATIONS

Imura et al., "An Immunoelectron Microscopic Study of Mycoplasma Hyosynoviae in Primary Swine Kiney Cell Culture". Kobe Journal of Medical Sciences, vol. 29, No. 1, 1983, pp. 1-15.

International Search Report and Written Opinion for PCT/US2013/076803 dated May 27, 2014.

Potgieter et al., "Chronological Development of Mycoplasma hyorhinis and Mycoplasma hyosynoviae Infections in Cultures of a Swine Synovial Cell Strain". Canadian Journal of Comparative Medicine-Revue Canadienne Demedecine Comparee, vol. 36, No. 2, Apr. 1972, pp. 145-149.

Volokhov et al., "Mycoplasma testing of cell substrates and biologics: Review of alternative non-microbiological techniques". Molecular and Cellular Probles, vol. 25, 2011, pp. 69-77.

Kobayashi et al., "Marolide Susceptibility of Mycoplasma hyorhinis Isolated from Piglets". Antimicrobial Agents and Chemotherapy, vol. 40, No. 4, Apr. 1995, pp. 1030-1032.

\* cited by examiner

IMMUNOGENIC COMPOSITION COMPRISING MYCOPLASMA ANTIGENS

BACKGROUND

Bacteria of the *Mycoplasma* genus belong to the class Mollicutes and represent a group of organisms that derived from the Firmicutes lineage. Mollicutes are the smallest autonomously replicating organisms, which differ structurally from other eubacteria in that they lack a cell wall. The surface of their single membrane is considered a key interface in mediating adaptation and survival in the context of a complex, immunocompetent host. Further, Mollicutes have a small genome and a limited number of metabolic pathways. Therefore, members of the *Mycoplasma* genus have also been portrayed as "minimal self-replicating organisms." However, despite this apparent simplicity, a large number of *mycoplasma* bacteria are pathogens of humans and a wide range of animals. In contrast to other pathogenic bacteria where virulence is mostly determined by toxins, invasins, and cytolysins, pathogenic *Mycoplasma* bacteria appear to have no such typical primary virulence factors (Chambaud, I. et al, 2001, *Nucleic Acids Res.* 29: 2145-2153, Fraser et al, 1995, *Science* 270: 397-403). There is currently little knowledge available on the molecular mechanisms and the effectors that allow pathogenic *mycoplasmas* to cause host cell damage, inflammation and disease.

Pathogenic *Mycoplasma* cause mainly atypical pneumonia, uro-genital infections and arthritis in humans and in animals (Blanchard, A., and G. F. Browning (eds.). 2005. *Mycoplasmas: Molecular biology, pathogenicity and strategies for control*. Horizon Bioscience, Wymondham U.K.; Kobisch M. and Friis N. F. 1996, Swine mycoplasmoses, *Rev. Sci. Tech. Off. Int. Epiz.* 15, 1569-1605). It is known that reactivation or exacerbation of the symptoms repeats and transfers gradually to a chronic disease, and thus along with early diagnosis and early treatment, prevention or treatment of exacerbation or reactivation are important. *M. hyopneumoniae* is the aetiological agent of enzootic pneumonia. In swine it is one of the most common and economically important diseases due to reduced weight gain and poor feed efficiency. The disease causes lesions in the lungs, a chronic cough, dull hair coat, retarded growth and unthrifty appearance lasting several weeks. The lung lesions, particularly in ventral apical and cardiac lobes, are characterized by a hyperplasia of the epithelial cells and an increased perivascular and peribronchiolar accumulation of mononuclear cells. *M. hyorhinis*, another common *mycoplasma* of the respiratory tract of pigs, can cause polyserositis and arthritis in piglets. *M. hyosynoviae* is generally located in the tonsils and can cause arthritic disease, leading to economic losses. *M. hyosynoviae* is isolated from the joints and pharyngeal/tonsillar samples and can induce antibodies in blood and joint fluid. *M. bovis* is considered to be one of the more pathogenic species of *Mycoplasma* and causes significant economic losses worldwide. Mycoplasmas cause severe clinical signs in cattle of all ages. *M. bovis* is the most frequent *Mycoplasma* pathogen found to cause pneumonia, mastitis, and arthritis in cattle and its etiological role has also been associated with otitis, keratoconjunctivitis, synovitis, and reproductive disorders in cows and bulls.

Because *mycoplasma* lack a cell wall, they are unaffected by many common antibiotics such as penicillin or other beta-lactam antibiotics that target cell wall synthesis. Therapeutic agents for *mycoplasma* infection that are in practical use are some antibiotics such as macrolide-based, or newquinolone-based, or tetracycline-based antibiotics, but such antibiotics have great adverse effects such as advent of drug-resistant strains, which leads the *mycoplasma* infection to become severe while sufficient treating effects are not expected, and becomes a cause for transfer to a chronic disease.

Further, vaccination is an effective method of controlling *mycoplasma* infection. Vaccines effective against several *mycoplasma* bacteria have been described in the prior art. WO2009058833 (A2) exemplary describes an attenuated, avirulent *Mycoplasma bovis* bacterium strain for vaccination. Further, WO2009126356 (A2) describes an immunogenic composition against *Mycoplasma hyopneumoniae*. However, what is needed are efficacious combination vaccines which provide protection against multiple pathogens. Such combination vaccines are very desirable in order to minimize the number of immunizations required to confer protection against multiple pathogens, to lower administration costs, and to increase acceptance and coverage rates. However, the problem of antigenic interference complicates the development of multi-component vaccines. Specifically, antigenic interference refers to the observation that administering multiple antigens often results in a diminished response to certain antigens relative to the immune response observed when such antigens are administered individually.

Thus, there is a need for efficacious combination vaccines which provide protection against multiple pathogens.

DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "a antigen" includes a plurality of antigens, reference to the "cell" is a reference to one or more cells and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art. Generally, the present invention provides an immunogenic composition comprising: a) one or more antigens of *M. hyosynoviae* and one or more antigens selected from the group consisting of *M. hyopneumoniae* and *M. hyorhinis*, and combinations thereof; and b) a pharmaceutically acceptable carrier.

Further, the present invention provides an immunogenic composition comprising: a) one or more antigens of *M. hyorhinis* and one or more antigens of *M. hyosynoviae*; and b) a pharmaceutically acceptable carrier.

Advantageously, the experimental data provided by the present invention disclose efficacy of the immunogenic composition provided herein and a lack of antigenic interference. Specifically, after administration of an immunogenic composition comprising antigens of *M. hyorhinis*, *M. hyopneumoniae* and *M. hyosynoviae* a lack of interference has been shown with regard to the efficacy of *M. hyorhinis* and *M. hyopneumoniae*.

Thus, according to one aspect, the present application provides an immunogenic composition comprising a) one or more antigens of *M. hyorhinis*; one or more antigens of *M. hyosynoviae*; b) one or more antigens of *M. hyopneumoniae*; and c) a pharmaceutically acceptable carrier.

The term "immunogenic composition" refers to a composition that comprises at least one antigen, which elicits an immunological response in the host to which the immunogenic composition is administered. Such immunological response can be a cellular and/or antibody-mediated immune response to the immunogenic composition of the invention. The host is also described as "subject". Preferably, any of the hosts or subjects described or mentioned herein is an animal.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "infection" or "infected" refer to the infection of a subject by a pathogen, i.e. *M. hyorhinis* or *M. hyorhinis* and *M. hyosynoviae* or *M. hyorhinis, M. hyopneumoniae* and *M. hyosynoviae*.

A "therapeutical response" will be demonstrated by a reduction of and/or cure of clinical signs normally displayed by a host when such host is already infected with a pathogen (e.g. *mycoplasma*) which normally causes such clinical sign or signs.

The term "*mycoplasma*" is known by the person skilled in the art. "*Mycoplasma*" refers to a genus of bacteria, e.g. as described in Blanchard, A., and G. F. Browning (eds.). 2005. *Mycoplasmas: Molecular biology, pathogenicity and strategies for control. Horizon Bioscience,* Wymondham U.K.; Kobisch M. and Friis N. F. 1996, *Swine mycoplasmoses, Rev. Sci. Tech. Off. Int. Epiz.* 15, 1569-1605. Bacteria can be classified based on their biochemical and microbiological properties as well as their morphology. These classification criteria are well known in the art. In general the *mycoplasma* infection is associated with the clinical signs described elsewhere in this description.

The term "*mycoplasma*" as used herein refers to *M. hyorhinis* or *M. hyorhinis* and *M. hyosynoviae* or *M. hyorhinis, M. hyopneumoniae* and *M. hyosynoviae*. Complete genome sequence of *M. hyorhinis* is exemplarily provided e.g. by Liu, W. et al., J. Bacteriol. 2010, vol. 192 (21), 5844-45 doi: 10.1128/JB.00946-10. Epub 2010 Aug. 27 or by Calcutt M J. et al., 2012, J. Bacteriol. Vol. 194 (7), 1848 doi: 10.1128/JB.00033-12. Isolates of *M. hyosynoviae* are exemplarily deposited at the American Tissue Culture Collection under accession numbers ATCC 25591 or ATCC 27095. Isolates of *Mycoplasma* hyopneumoniae are exemplarily deposited at the American Tissue Culture Collection under accession numbers ATCC 25095, ATCC 25617, and ATCC 25934. The genomic DNA of *Mycoplasma* hyopneumoniae J-strain is deposited at the American Tissue Culture Collection under accession numbers ATCC 25934D.

An "antigen" as used herein refers to, but is not limited to, components which elicit an immunological response in a host to an immunogenic composition or vaccine of interest comprising such antigen or an immunologically active component thereof. The antigen or immunologically active component can be a whole microorganism (in inactivated or modified live form), or any fragment or fraction thereof, which, if administered to a host, can elicit an immunological response in the host. The antigen can be or can comprise complete live organisms in either its original form or as attenuated organisms in a so called modified live vaccine (MLV). The antigen can further comprise appropriate elements of said organisms (subunit vaccines) whereby these elements are generated either by destroying the whole organism or the growth cultures of such organisms and subsequent purification steps yielding in the desired structure(s), or by synthetic processes induced by an appropriate manipulation of a suitable system like, but not restricted to bacteria, insects, mammalian or other species, and optionally by subsequent isolation and purification procedures, or by induction of said synthetic processes in the animal needing a vaccine by direct incorporation of genetic material using suitable pharmaceutical compositions (polynucleotide vaccination). The antigen can comprise whole organisms inactivated by appropriate methods in a so called killed vaccine (KV). If the organism is a bacterium, the killed vaccine is called a bacterin.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

In one aspect of the present invention one or more of the antigens are whole inactivated bacterins. The one or more whole inactivated antigens can be whole inactivated bacterin selected from the group consisting of: *M. hyorhinis; M. hyosynoviae; M. hyopneumoniae; M. hyorhinis* and *M. hyosynoviae;* and *M. hyorhinis, M. hyopneumoniae* and *M. hyosynoviae*.

Thus, according to one aspect, the present application provides an immunogenic composition comprising a) one or more antigens of *M. hyorhinis;* and one or more antigens of *M. hyosynoviae;* and b) a pharmaceutically acceptable carrier, wherein the *M. hyorhinis; M. hyosynoviae;* or the *M. hyorhinis* and *M. hyosynoviae* antigens are whole inactivated bacterins.

According to another aspect, the present application provides an immunogenic composition comprising a) one or more antigens of *M. hyorhinis;* one or more antigens of *M. hyosynoviae* and one or more antigens of *M. hyopneumoniae* b) a pharmaceutically acceptable carrier, wherein the *M. hyorhinis; M. hyosynoviae;* and/or the *M. hyopneumoniae* antigens are whole inactivated bacterins. This aspect of the present invention encompasses that either the *M. hyorhinis* antigen is a whole inactivated bacterin or the *M. hyopneumoniae* antigen is a whole inactivated bacterin or the *M. hyosynoviae* antigen is a whole inactivated bacterin. However, this aspect of the present invention also encompasses that all antigens in the immunogenic composition according to the present invention are whole inactivated bacterins, i.e. *M. hyorhinis* and *M. hyosynoviae* antigens or *M. hyorhinis, M. hyopneumoniae* and *M. hyosynoviae* antigens are whole inactivated bacterins.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation can also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the *mycoplasma* species. In general, the inaction process is performed until no *mycoplasma* growth can be detected in a suitable cultivation system.

In one aspect of the present invention the whole inactivated bacterins are formalin inactivated bacterins, preferably using the concentrations as described hereinabove. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein one or more antigens are whole inactivated bacterins and wherein one or more of the whole inactivated bacterins are formalin inactivated bacterins. According to a further aspect, such immunogenic composition further comprises one or more antigens of *M. hyopneumoniae*. This aspect of the present invention encompasses that either the *M. hyorhinis* antigen is a formalin inactivated bacterin or the *M. hyopneumoniae* antigen is a formalin inactivated bacterin or the *M. hyosynoviae* antigen is a formalin inactivated bacterin. However, this aspect of the present invention also encompasses that all *mycoplasma* antigens in the immunogenic composition according to the present invention are formalin inactivated bacterins, i.e. *M. hyorhinis* and *M. hyosynoviae* antigens or *M. hyorhinis* and *M. hyopneumoniae* and *M. hyosynoviae* antigens are formalin inactivated bacterins.

The inactivated bacterin component of the invention can be incorporated into liposomes using known technology such as that described in *Nature*, 1974, 252, 252-254 or *Journal of Immunology*, 1978, 120, 1109-13. In another embodiment of the invention, the inactivated bacterin component of the invention can be conjugated to suitable biological compounds such as polysaccharides, peptides, proteins, or the like, or a combination thereof.

In a further aspect, the immunogenic composition as provided herewith is effective in the treatment and/or prophylaxis of clinical signs caused by *M. hyorhinis* in a subject of need. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein such immunogenic composition is effective in the treatment and/or prophylaxis of clinical signs caused by *M. hyorhinis* in a subject of need. According to a further aspect, such immunogenic composition further comprises one or more antigens of *M. hyopneumoniae*. According to a further aspect, the one or more *mycoplasma* antigens is/are whole inactivated bacterins of such *mycoplasma* species as described hereinabove.

In a further aspect, the immunogenic composition as provided herewith and which also comprises one or more antigens of *M. hyopneumoniae* is effective in the treatment and/or prophylaxis of clinical signs caused by *M. hyopneumoniae* in a subject of need. Thus, according to one aspect, the present application provides an immunogenic composition comprising a) one or more antigens of *M. hyorhinis*; one or more antigens of *M. hyosynoviae*; b) one or more antigens of *M. hyopneumoniae*; and c) a pharmaceutically acceptable carrier, wherein such immunogenic composition is effective in the treatment and/or prophylaxis of clinical signs caused by *M. hyopneumoniae* in a subject of need. According to a further aspect, such immunogenic composition is effective in the treatment and/or prophylaxis of clinical signs caused by *M. hyorhinis* and *M. hyopneumoniae* in a subject of need. According to a further aspect, the one or more *mycoplasma* antigens is/are whole inactivated bacterins of such *mycoplasma* species as described hereinabove.

The term "treatment and/or prophylaxis" refers to the lessening of the incidence of the particular *mycoplasma* infection in a herd or the reduction in the severity of clinical signs caused by or associated with the particular *mycoplasma* infection. Thus, the term "treatment and/or prophylaxis" also refers to the reduction of the number of animals in a herd that become infected with the particular *mycoplasma* bacteria (=lessening of the incidence of the particular *mycoplasma* infection) or to the reduction of the severity of clinical signs normally associated with or caused by a *mycoplasma* infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to a subject or herd of subjects in need of or that could benefit from such a treatment/prophylaxis. The term "treatment" refers to the administration of the effective amount of the immunogenic composition once the subject or at least some animals of the herd is/are already infected with such *mycoplasma* and wherein such animals already show some clinical signs caused by or associated with such *mycoplasma* infection. The term "prophylaxis" refers to the administration of a subject prior to any infection of such subject with *mycoplasma* or at least where such animal or none of the animals in a group of animals do not show any clinical signs caused by or associated with the infection by such *mycoplasma*.

The term "an effective amount" as used herein means, but is not limited to an amount of antigen, that elicits or is able to elicit an immune response in a subject. Such effective amount is able to lessen the incidence of the particular *mycoplasma* infection in a herd or to reduce the severity of clinical signs of the particular *mycoplasma* infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to subjects that are either not treated or treated with an immunogenic composition that was available prior to the present invention but subsequently infected by the particular *mycoplasma* bacteria.

The term "clinical signs" as used herein refers to signs of infection of a subject from *mycoplasma* bacteria. The clinical signs of infection depend on the pathogen selected. Examples for such clinical signs include but are not limited to respiratory distress, polyserositis (such as peritonitis, pleuritis, pericarditis), arthritis (lameness and swollen joints), otitis, roughened hair coat, slight fever, depression, reduced appetite, and bacteremia. However, the clinical signs also include but are not limited to clinical signs that are directly observable from a live animal. Examples for clinical signs that are directly observable from a live animal include nasal and ocular discharge, lethargy, coughing, wheezing, thumping, elevated fever, weight gain or loss, dehydration, diarrhea, joint swelling, lameness, wasting, paleness of the skin, unthriftiness, diarrhea, and the like.

Reduction in the incidence of or reduction of the severity of clinical signs caused by or being associated with the particular *mycoplasma* infection in a subject can be reached by the administration of one or more doses of the immunogenic composition of the present invention to a subject in need. As demonstrated by the Examples 2 and 3, the immunogenic composition as provided herein has been proven to be efficacious after the administration of a single dose to a subject of need. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein such immunogenic composition is effective in the treatment and/or prophylaxis of clinical signs caused by *M. hyorhinis* in a subject of need after the administration of a single dose. Such single dose is only administered once. According to a further aspect, such immunogenic composition further comprises one or more antigens of *M. hyopneumoniae*. According to a further aspect, the one or more *mycoplasma* antigens are whole inactivated bacterins of such *mycoplasma* species as described hereinabove.

It has furthermore been shown that one dose of the immunogenic composition which comprises *M. hyopneumoniae* is also effective after the administration of such single dose of such immunogenic composition. Thus, according to one aspect, the present application provides an immunogenic composition comprising a) one or more antigens of *M. hyorhinis*; one or more antigens of *M. hyosynoviae*; b) one or more antigens of *M. hyopneumoniae*; and c) a pharmaceutically acceptable carrier, wherein such immunogenic composition is effective in the treatment and/or prophylaxis of clinical signs caused by *M. hyopneumoniae* in a subject of need after the administration of a single dose. Such single dose is only administered once. According to a further aspect, such immunogenic composition is effective in the treatment and/or prophylaxis of clinical signs caused by *M. hyorhinis* and *M. hyopneumoniae* in a subject of need. According to a further aspect, the one or more *mycoplasma* antigens is/are whole inactivated bacterins of such *mycoplasma* species as described hereinabove.

In one aspect of the present invention the immunogenic composition is prepared for the administration of a single-dose of such immunogenic composition. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the immunogenic composition is prepared for a the administration as a single-dose of such immunogenic composition. Such immunogenic composition can also comprise one or more antigens of *M. hyopneumoniae*, wherein such immunogenic composition that comprises a) one or more antigens of *M. hyorhinis* and one or more antigens of *M. hyosynoviae*; b) one or more antigens of *M. hyopneumoniae*; and c) a pharmaceutically acceptable carrier, are prepared or provided for a single-dose administration. According to a further aspect, one or more of the *mycoplasma* antigens can be whole inactivated bacterins of such *mycoplasma* species as described herein. Furthermore, such immunogenic composition is effective in the treatment and/or prophylaxis of clinical signs caused by *M. hyorhinis* or *M. hyorhinis* and *M. hyopneumoniae* in a subject of need after the administration of a single dose of such *mycoplasma* antigens, each depending on whether the composition comprises on or more antigens of *M. hyopneumoniae* or not. Advantageously, the experimental data provided by the present invention disclose that a single dose administration of the immunogenic composition of the present invention reliably and effectively stimulated a protective immune response. Specifically, a measurable antibody response has been shown for *M. hyorhinis* and *M. hyopneumoniae*.

As mentioned above, the term subject or host as used herein relates to animals, preferably to mammals such as mice, rats, guinea pigs, rabbits, hamsters, swine, sheep, dogs, cats, horses, monkeys, or cattle and, also preferably, to humans.

Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the immunogenic composition is effective in the treatment and/or prophylaxis of clinical signs caused by *M. hyorhinis* in a swine. According to a further aspect, such immunogenic composition is effective in the treatment and/or prophylaxis of clinical signs caused by *M. hyorhinis* in swine. When such immunogenic composition further comprises one or more antigens of *M. hyopneumoniae*, it is, according to a further aspect effective in the treatment and/or prophylaxis of clinical signs caused by *M. hyopneumoniae* in swine. According to a further aspect, such immunogenic composition, which comprises one or more antigens of *M. hyorhinis* and *M. hyopneumoniae* is effective in the treatment and/or prophylaxis of clinical signs caused by *M. hyorhinis* and *M. hyopneumoniae* in swine. Again, the one or more of the *mycoplasma* antigens can be whole inactivated bacterins of such *mycoplasma* species as described hereinabove.

In a further aspect of the present invention the immunogenic composition is a vaccine. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the immunogenic composition is a vaccine. Such vaccine can also comprise one or more antigens of *M. hyopneumoniae*. The vaccine according to the invention, when administered to a subject in need, has the same beneficial properties as described for the immunogenic compositions.

In one aspect of the present invention the pharmaceutical-acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the pharmaceutical-acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof. As mentioned above, such vaccine can also comprise one or more antigens of *M. hyopneumoniae*. Furthermore, the one or more *mycoplasma* antigens of such *mycoplasma* species can be provided as whole inactivated bacterin as described herein above.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others. Among the copolymers of maleic anhydride and alkenyl derivative, the copolymers EMA (Monsanto), which are copolymers of maleic anhydride and ethylene, are included. The dissolution of these polymers in water leads to an acid solution that will be neutralized, preferably to physiological pH, in order to give the adjuvant solution into which the immunogenic, immunological or vaccine composition itself will be incorporated.

In one aspect of the present invention the pharmaceutical-acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymer, SAF-M, monophosphoryl lipid A, Avridine lipid-amine, heat-labile enterotoxin from *E. coli* (recombinant or otherwise), cholera toxin, IMS 1314, muramyl dipeptide, and combinations thereof. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the pharmaceutical-acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, the RIBI adjuvant system, Block co-polymer, SAF-M, monophosphoryl lipid A, Avridine lipid-amine, heat-labile enterotoxin from *E. coli* (recombinant or otherwise), cholera toxin, IMS 1314, muramyl dipeptide, and combinations thereof. Such vaccine can also comprise one or more antigens of *M. hyopneumoniae*. Furthermore, one or more of the *mycoplasma* antigens of such *mycoplasma* species can be provided as whole inactivated bacterin as described herein above.

A further example of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are polymers of acrylic acid cross-linked with polyalkenyl ethers or divinyl glycol or cross-linked with an allyl sucrose or with allyl pentaerythritol. Among them, there may be mentioned CARBOPOL® 974P, 934P and 971P. Most preferred is the use of CARBOPOL® 971P.

Preferably, the adjuvant is added in an amount of about 100 µg to about 10 mg per dose. Even more preferably the adjuvant is added in an amount of about 100 µg to about 10 mg per dose. Still more preferably the adjuvant is added in an amount of about 500 µg to about 5 mg per dose. Still more preferably the adjuvant is added in an amount of about 750 µg to about 2.5 mg per dose. Most preferably the adjuvant is added in an amount of about 1 mg per dose.

In one aspect of the present invention the pharmaceutically acceptable carrier is a water-in-oil-in-water emulsion or a carbomer. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the pharmaceutically acceptable carrier is a water-in-oil-in-water emulsion or a carbomer. Such vaccine can also comprise one or more antigens of *M. hyopneumoniae*. Furthermore, the antigens of such *mycoplasma* species can be provided as whole inactivated bacterin as described herein above.

In one aspect of the present invention the water-in-oil-in-water emulsion is Montanide ISA207 VG or CARBOPOL®. Montanide ISA207 VG is an adjuvant composed of oleic esters of anhydrous mannitol in solution in a non mineral oil and is designed to achieve water-in-oil-in-water vaccine emulsions. Montanide ISA207 VG is well known to the person skilled in the art. Thus, according to one aspect, the present application provides an immunogenic composition comprising a) one or more antigens of *M. hyorhinis*; and one or more antigens of *M. hyosynoviae*; and b) a pharmaceutically acceptable carrier, wherein the pharmaceutically acceptable carrier is Montanide ISA207 VG or CARBOPOL®. As mentioned above, such vaccine can also comprise one or more antigens of *M. hyopneumoniae*. Furthermore, the antigens of such *mycoplasma* species can be provided as whole inactivated bacterin as described herein above.

The present invention also provides immunogenic composition obtained by a method comprising a) cultivation of *mycoplasma* bacteria selected from the group consisting of *M. hyorhinis*, *M. hyopneumoniae* and *M. hyosynoviae* in a serum-reduced, eukaryotic cell system; b) obtaining one or more antigens of such *mycoplasma* bacteria; and c) addition of a pharmaceutically acceptable carrier.

The term "cultivation" is known by the person skilled in the art. The term relates to the propagation of cells in culture outside the organism. Particularly, the term "cultivation" relates to the propagation of cells outside the organism in a cell system.

The term "cell system" is known by the person skilled in the art. In particular, the term "cell system" is an in vitro cell culture system for the cultivation of microorganism, such as e.g. *mycoplasma* bacteria. Such cell system comprises host cells and cell culture medium suitable for the propagation of such cells outside of the organism. In particular, the host cells, may or may not be susceptible for an infection with the *mycoplasma* bacteria. Such host cells can be present as live cells, in inactivated form or as cell fragments. Preferably, such host cells are susceptible for an infection with the *mycoplasma* bacteria. Host cells that can be used to practice the method as described herein include but are not limited to Madin-Darby Canine Kidney Epithelial (MDCK) cells (e.g. Madin-Darby Canine Kidney Epithelial Cells as deposited with the American Tissue Culture Collection under accession number ATCC CCL-34 or ATCC CRL-2285) or McCoy cells (e.g. as deposited with the American Tissue Culture Collection under accession number ATCC CRL-1696). Suitable cell culture media are known to a person skilled in the art and are commercially available. They can comprise nutrients, salts, growth factors, antibiotics, serum (e.g. fetal calf serum) and pH-indicators (e.g. phenol red).

The term "eukaryotic cell system" comprises primary eukaryotic cells and eukaryotic cells derived from multicellular organisms such as plants or animals. Furthermore, the eukaryotic cell system encompasses eukaryotic single cell organisms (also referred to as microorganisms), e.g. bacteria or fungi including yeast. However, it is understood the eukaryotic cells are different from *mycoplasma* bacteria.

The term "serum reduced" refers to a reduced amount of serum that is added for the cultivation of *mycoplasma* bacteria in the eukaryotic cell system compared to the amount of serum that is used for the cultivation of *mycoplasma* bacteria of the same species in a cell free cultivation system. The amount of serum for the cultivation of *mycoplasma* bacteria in the eukaryotic cell system compared to the amount of serum for the cultivation of *mycoplasma* bacteria in a cell free cultivation system is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95%, even more preferably by at least 96%, even more preferably by at least 97%, even more preferably by at least 98%, even more preferably by at least 99%, most preferably by 100%. Thus, it has to be understood that according to the present invention the *mycoplasma* bacteria are most preferably cultivated in a eukaryotic cell system lacking any serum.

The term "cell free cultivation system" as used herein refers to cultivation system that does not include any cells except of the *mycoplasma* bacteria.

Preferred amounts of serum for the cultivation of *mycoplasma* bacteria in the eukaryotic cell system include serum concentrations between about 0-10% (v/v), more preferably from about 1-9% (v/v), still more preferably from about 1-8% (v/v), even more preferably from about 1-7% (v/v), even more preferably from about 1-6% (v/v), and most preferably about 2-5% (v/v).

Preferred amounts of serum for the cultivation of *mycoplasma* bacteria in the eukaryotic cell system comprising MDCK cells include serum concentration between about 0-6% (v/v), more preferably from about 1-5% (v/v), still more preferably from about 2-4% (v/v), even more preferably from about 2-3% (v/v), and most preferably about 2% (v/v).

Preferred amounts of serum for the cultivation of *mycoplasma* bacteria in the eukaryotic cell system comprising McCoy cells include serum concentration between about 0-10% (v/v), more preferably from about 1-9% (v/v), still more preferably from about 2-8% (v/v), even more preferably from about 3-7% (v/v), even more preferably from about 4-6% (v/v), and most preferably about 5% (v/v).

In accordance with the present invention it has to be understood that the eukaryotic cells of the eukaryotic cell system can be infected with *mycoplasma* bacteria. Such infection results in a propagation of the *mycoplasma* bacteria within the eukaryotic cell system. The infection of eukaryotic cells by *mycoplasma* bacteria and the conditions of the post incubation period to allow the propagation of the *mycoplasma* bacteria are well known to the person skilled in the art. However, preferably, post transfection the cells are incubated over a period of up to 21 days, more preferably from about two days to about fourteen days, more preferably from about two days to about eight days, still more preferably from about three to five days. Preferred incubation conditions include a temperature between about 32-42° C., more preferably from about 34-40° C., still more preferably from about 35-39° C., even more preferably from about 36-38° C., and most preferably about 37° C. Preferred incubation conditions also include a $CO_2$-concentration between about 2% to 8%, more preferably from about 3% to 7% even more preferably from about 4% to 6%, and most preferably about 5%. Preferably, the eukaryotic cells are observed following transfection for characteristic changes, such as cell density trends, the decrease in viability including cytophatic effects during the post-infection period and the color change of the medium due to pH-changes.

The term "obtaining" comprises the harvest, isolation, purification and/or formulation (e.g. inactivation and/or blending) of the antigen.

The term "harvest" refers to collecting or recovering the antigen of the *mycoplasma* bacteria from the transfected eukaryotic cell system. Any conventional method known in the art can be used to recover said *mycoplasma* antigen, e.g. any separation method. Well known methods in the art comprise centrifugation or filtration, such as using a semi-permeable membrane having a certain pore size.

The term "isolation" comprises an isolation step of the *mycoplasma* antigen. Methods for the isolation of antigens of the *mycoplasma* bacteria from the infected eukaryotic cell system are known to a person skilled in the art. Those methods comprise physical and/or chemical methods, including but are not limited to freeze thaw cycles, treatment with ultrasound and the alike.

Methods for the "purification" of antigens from the isolate are known to a person skilled in the art, for example by those methods described in Protein purification methods—a practical approach (E. L. V. Harris and S. Angal, eds., *IRL Press at Oxford University Press*). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The antigen can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein can also include further finishing steps like the addition of buffer, inactivation, neutralization steps and the alike.

Thus, according to one aspect, the present invention provides an immunogenic composition, that comprises one or more *mycoplasma* antigens selected from the group of *M. hyorhinis, M. hyopneumoniae, M. hyosynoviae* and any combinations thereof, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyorhinis*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyosynoviae*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyopneumoniae*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyorhinis* and *M. hyopneumoniae*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyorhinis* and *M. hyosynoviae*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyopneumoniae* and *M. hyosynoviae*, wherein one or more of the *mycoplasma* antigens are produced in a serum-reduced, eukaryotic cell system. According to a further aspect, all of the *mycoplasma* antigens are produced in a serum-reduced, eukaryotic cell system.

Thus, according to one aspect, the present invention provides an immunogenic composition that comprises one or more *mycoplasma* antigens of *M. hyorhinis*, *M. hyopneumoniae*, and *M. hyosynoviae*, wherein one or more of the *mycoplasma* antigens are produced in a serum-reduced, eukaryotic cell system. According to a further aspect, all of the *mycoplasma* antigens are produced in a serum-reduced, eukaryotic cell system.

The one or more *mycoplasma* antigens is/are inactivated, preferably by any of the methods as described hereinabove. According to a further aspect, all of the *mycoplasma* antigens are inactivated, preferably, by any of the methods as described hereinabove. Thus, according to a further aspect the present invention provides immunogenic composition prepared by a method comprising a) cultivation of *mycoplasma* bacteria selected from the group consisting of *M. hyorhinis*, *M. hyopneumoniae*, *M. hyosynoviae*, and any combinations thereof in a serum-reduced, eukaryotic cell system; b) obtaining one or more antigens of such *mycoplasma* bacteria wherein the obtaining step includes the inactivating of one or more of the *mycoplasma* antigens; and c) addition of a pharmaceutically acceptable carrier. The inactivation step can be performed by any of the method as described hereinabove. According to one aspect, such inactivation results in whole inactivated bacterins of the *mycoplasma* bacteria. Preferably, such inactivation of the *mycoplasma* bacteria is done by formalin such that the *mycoplasma* antigen is whole formalin inactivated bacterin. In one aspect, the inactivated *mycoplasma* antigens are whole inactivated bacterin of *M. hyorhinis*, whole inactivated bacterin of *M. hyopneumoniae*, whole inactivated bacterin of *M. hyosynoviae*, whole inactivated bacterin of *M. hyorhinis* and *M. hyosynoviae* or whole inactivated bacterin of *M. hyopneumoniae* and *M. hyosynoviae*, or whole inactivated bacterin of *M. hyorhinis* and *M. hyopneumoniae* or whole inactivated bacterin of *M. hyorhinis*, *M. hyopneumoniae* and *M. hyosynoviae*. According to a further aspect, all of the *mycoplasma* antigens within the immunogenic composition are whole inactivated bacterins, preferably whole formalin inactivated bacterins.

In one aspect, the *mycoplasma* antigen is produced in a serum-reduced, eukaryotic cell system, wherein the serum is free swine serum. As the *mycoplasma* bacteria *M. hyorhinis*, *M. hyopneumoniae* and *M. hyosynoviae* are swine pathogens, serum of swine may comprise components which can interfere with the *mycoplasma* antigens of the composition of the present invention, such that the use of non-swine serum or of no serum is a preferred aspect of the invention. Thus, according to one aspect, the present application provides an immunogenic composition obtained by a method comprising a) cultivation of a *mycoplasma* bacteria selected from the group consisting of *M. hyorhinis*, *M. hyopneumoniae*, *M. hyosynoviae* and any combinations thereof in a serum-reduced, eukaryotic cell system; b) obtaining an antigen of such *mycoplasma* bacteria; and c) addition of a pharmaceutically acceptable carrier, wherein the eukaryotic cell system is free of swine serum.

As mentioned hereinabove, the eukaryotic cell system can comprise cells of MDCK cell line or a McCoy cell line. Thus, according to one aspect, the present application provides a method for the preparation of an immunogenic composition, wherein the method comprises a) cultivation of a *mycoplasma* bacteria selected from the group consisting of *M. hyorhinis*, *M. hyopneumoniae*, *M. hyosynoviae*, and any combinations thereof in a serum-reduced, eukaryotic cell system; b) obtaining an antigen of such *mycoplasma* bacteria; and c) addition of a pharmaceutically acceptable carrier, wherein the eukaryotic cell system comprises a MDCK cell line or a McCoy cell line.

In a further aspect, the *mycoplasma* antigen of the immunogenic composition is produced in a serum-reduced, eukaryotic cell system, wherein the said *mycoplasma* antigen has an increased immunogenicity compared to the same antigen obtained from *mycoplasma* cultivated in a cell free culturing system.

The term "increased immunogenicity" as used herein, means that the immunological response caused by an immunogenic composition comprising an antigen of interest is increased as compared to a reference immunogenic composition comprising the same antigen, wherein the antigen of the reference immunogenic composition is prepared of *mycoplasma* bacteria cultivated in a cell free culturing system.

The term "increased" means, that the cellular and/or antibody mediated immune response is increased by at least 10%, preferably by at least 20%, more preferably by at least 30%, even more preferably by at least 40%, even more preferably by at least 50%, even more preferably by at least 75%, most preferably by at least 100% as compared to the cellular and/or antibody mediated immune response elicited by a reference immunogenic composition comprising the same antigen, wherein the antigen of the reference immunogenic composition is prepared of *mycoplasma* bacteria cultivated in a cell free culturing system. It is in the general knowledge of a person skilled in the art how to measure the cellular and/or antibody mediated immune response. In particular, it is clear to such person skilled in the art either to compare the cellular mediated immune response of the immunogenic composition of interest with cellular mediated immune response of the reference, or the antibody mediated immune response of the immunogenic composition of interest with that of the reference composition, but neither the cellular mediated immune response of a immunogenic composition of interest with the antibody mediated immune response of the reference or vice versa. Moreover, the cellular mediated immune response can be measured, for example, by measuring the activation of cytotoxic T-cells by an immunogenic composition/antigen of interest. The antibody mediated immune response can be measured, for example, by measuring the amount of antigen specific antibodies, generated in cause of the administration of the immunogenic composition comprising such antigen to an animal. The cellular and/or antibody mediated immune response can be measured, for example, by using a mouse model, a cat model, a cattle model or a swine model. However, the assays as described in Examples 4 and 5 shall be used as a reference assay for detecting the immunological response against *M. hyorhinis* and *M. hyopneumoniae*.

The term "same antigen" means, that nature of the antigens is identical. Thus, if the *mycoplasma* antigen of the immunogenic composition produced in a serum-reduced, eukaryotic cell system is whole inactivated bacterin of *M. hyorhinis*, than the "same antigen" means that the *mycoplasma* antigen of the cell-free system is also whole inactivated bacterin of *M. hyorhinis*. Furthermore, if the *mycoplasma* antigen of the immunogenic composition produced in a serum-reduced, eukaryotic cell system prepared or purified according to a specific method, than the same antigen means that the *mycoplasma* antigen of the cell-free system is prepared or purified according to the same method.

Advantageously, the experimental data provided by the present invention disclose that *mycoplasma* antigens provided by the above described method have an increased immunogenicity compared to antigens obtained from *mycoplasma* bacteria cultivated in a cell free culturing system Specifically, MDCK-based *M. hyorhinis* vaccines showed earlier on-set of sero-conversion, greater number of sero-positive pigs and higher serological titers.

Thus, according to one aspect, the present application provides an immunogenic composition obtained by a method comprising a) cultivation of a *mycoplasma* bacteria selected from the group consisting of *M. hyorhinis, M. hyopneumoniae, M. hyosynoviae* and any combinations thereof in a serum-reduced, eukaryotic cell system; b) obtaining an antigen of such *mycoplasma* bacteria; and c) addition of a pharmaceutically acceptable carrier, wherein said immunogenic composition has an increased immunogenicity compared to an immunogenic composition comprising the same antigen obtained from *mycoplasma* cultivated in a cell free culturing system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyosynoviae*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyopneumoniae*, wherein one or more of the *mycoplasma* antigens are produced in a serum-reduced, eukaryotic cell system wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis* and *M. hyopneumoniae*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis* and *M. hyosynoviae*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyopneumoniae* and *M. hyosynoviae*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis, M. hyopneumoniae*, and *M. hyosynoviae*, wherein one or more of the *mycoplasma* antigens are produced in a serum-reduced, eukaryotic cell system, wherein said immunogenic composition has an increased immunogenicity compared to an immunogenic composition comprising the same antigen obtained from *mycoplasma* cultivated in a cell free culturing system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

In a further aspect, the *mycoplasma* antigens is/are produced in a serum-reduced, eukaryotic cell system, wherein the immunogenic composition comprises components of the eukaryotic cells of said eukaryotic cell system.

The term "components of the eukaryotic cells" comprises both whole cells and fragments of said eukaryotic cells. The term "fragment" comprises any parts of the eukaryotic cell such as parts of the cell membrane or intracellular organelles as a whole or parts thereof. However, the term fragment also encompasses any part of said eukaryotic cell comprising lipids, proteins, sugars, DNA, RNA and the alike as well as combinations thereof. Further, the components of the eukaryotic cells and the *mycoplasma* antigen can either be in the immunogenic composition separately or attached to each other or a combination thereof.

Thus, according to one aspect, the present application provides an immunogenic composition obtained by a method comprising a) cultivation of a *mycoplasma* bacteria selected from the group consisting of *M. hyorhinis, M. hyopneumoniae, M. hyosynoviae* and any combinations thereof in a serum-reduced, eukaryotic cell system; b) obtaining an antigen of such *mycoplasma* bacteria; and c) addition of a pharmaceutically acceptable carrier, wherein the immunogenic composition comprises components of the eukaryotic cells of said eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis*, wherein one or more of the *mycoplasma* antigens are produced in a serum-reduced, eukaryotic cell system, wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyosynoviae*, wherein one or more of the *mycoplasma* antigens are produced in a serum-reduced, eukaryotic cell system, wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyopneumoniae*, wherein one or more of the *mycoplasma* antigens are produced in a serum-reduced, eukaryotic cell system wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis* and *M. hyopneumoniae*, wherein one or more of the *mycoplasma* antigens are produced in a serum-reduced, eukaryotic cell system, wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis* and *M. hyosynoviae*, wherein one or more of the *mycoplasma* antigens are produced in a serum-reduced, eukaryotic cell system wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyopneumoniae* and *M. hyosynoviae*, wherein one or more of the *mycoplasma* antigens are produced in a serum-reduced, eukaryotic cell system, wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis*, *M. hyopneumoniae*, and *M. hyosynoviae*, wherein one or more of the *mycoplasma* antigens are produced in a serum-reduced, eukaryotic cell system, wherein the immunogenic composition comprises components of the eukaryotic cells of said eukaryotic cell system. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

In a further aspect, the *mycoplasma* antigen is/are produced in a serum-reduced, eukaryotic cell system, wherein said components of the eukaryotic cells are attached to the *mycoplasma* antigen.

The term "attached" refers to any interaction, association, binding, adhering or linking of said components of the eukaryotic cells to the *mycoplasma* antigen. Thus, the term "attached" encompasses any interactions including indirect or direct, non-reversible or reversible, physical and chemical, electrostatic, and/or covalent bonds. Thus, it has to be understood that the components of the eukaryotic cells for example can be bound to the *mycoplasma* antigen. However, it has to be understood that the components of the eukaryotic cells can also be linked to the *mycoplasma* antigen. Such linking can be produced by several methods well known to the person skilled in the art such as formaldehyde treatment and the like.

Thus, according to one aspect, the present application provides an immunogenic composition obtained by a method comprising a) cultivation of a *mycoplasma* bacteria selected from the group consisting of *M. hyorhinis*, *M. hyopneumoniae*, *M. hyosynoviae* and any combinations thereof in a serum-reduced, eukaryotic cell system; b) obtaining an antigen of such *mycoplasma* bacteria; and c) addition of a pharmaceutically acceptable carrier, wherein said components of the eukaryotic cells are attached to the *mycoplasma* antigen. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyosynoviae*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyopneumoniae*, wherein one or more of the *mycoplasma* antigens are produced in a serum-reduced, eukaryotic cell system wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis* and *M. hyopneumoniae*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis* and *M. hyosynoviae*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyopneumoniae* and *M. hyosynoviae*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Thus, according to one aspect, the present invention provides an immunogenic composition that comprises one or more *mycoplasma* antigens of *M. hyorhinis, M. hyopneumoniae*, and *M. hyosynoviae*, wherein one or more of the *mycoplasma* antigens are produced in a serum-reduced, eukaryotic cell system, wherein said components of the eukaryotic cells are attached to the *mycoplasma* antigen. According to a further aspect, all of the *mycoplasma* antigens are produced in a serum-reduced, eukaryotic cell system. Furthermore, according to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin. According to a further aspect, all of the *mycoplasma* antigens are inactivated bacterins, preferably, formalin inactivated bacterins.

Again, the present invention provides an immunogenic composition that comprises one or more *mycoplasma* antigens selected from the group consisting of *M. hyorhinis, M. hyopneumoniae, M. hyosynoviae* and any combinations thereof, wherein one or more of the *mycoplasma* antigens are obtained from a serum-reduced, eukaryotic cell system. Thus, according to a further aspect, the present invention provides an immunogenic composition that comprises one or more antigens selected from the group consisting of *M. hyorhinis, M. hyopneumoniae* and *M. hyosynoviae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyosynoviae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyopneumoniae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis* and *M. hyopneumoniae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis* and *M. hyosynoviae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyopneumoniae* and *M. hyosynoviae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

Thus, according to one aspect, the present invention provides an immunogenic composition that comprises one or more *mycoplasma* antigens of *M. hyorhinis, M. hyopneumoniae*, and *M. hyosynoviae*; and one or more components of a eukaryotic cell system. According to a further aspect one or more of the *mycoplasma* antigens are whole inactivated bacterin. Such whole inactivated bacterin can be obtained by the inactivation methods as described herein. Preferably, such whole inactivated bacterin is formalin inactivated bacterin.

The present invention also relates to a method for immunizing a subject, comprising administering to a subject any of the immunogenic compositions as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular *mycoplasma* infection in a herd or in the reduction in the severity of clinical signs caused by or associated with the particular *mycoplasma* infection.

According to a further aspect, the present invention provides a method of immunizing a subject with any one of the immunogenic compositions provided herewith, comprising administering to such subject an immunogenic composition according to the invention.

Such immunogenic composition comprises a) one or more antigens of *M. hyosynoviae* and one or more antigens selected from the group consisting of *M. hyopneumoniae* and *M. hyorhinis* and the combination thereof; and b) a pharmaceutically acceptable carrier.

According to a further aspect, the immunogenic composition according to the invention comprises: a) one or more antigens of *M. hyorhinis* and one or more antigens of *M. hyosynoviae*; and b) a pharmaceutically acceptable carrier. According to a further aspect, the immunogenic composition also comprises one or more antigens of *M. hyopneumoniae*.

If the immunogenic composition is produced in a serum-reduced, eukaryotic cell system as described herein, then the immunogenic composition can in general comprise one or more antigens of a *mycoplasma* bacterium selected from the group consisting of *M. hyorhinis, M. hyopneumoniae, M. hyosynoviae* and any combination thereof as further defined herein.

According to a further aspect defined hereinabove, such immunogenic composition can comprise one or more components of a eukaryotic cell system in addition to the one or more antigens of a *mycoplasma* bacterium selected from the group consisting of *M. hyorhinis, M. hyopneumoniae, M. hyosynoviae* and any combination thereof.

According to a further aspect the one or more of the *mycoplasma* antigens used for immunizing the subject in need is/are whole inactivated bacterin. This aspect of the present invention encompasses that either one of the *mycoplasma* antigens is a whole inactivated bacterin. However, this aspect of the present invention also encompasses that all antigens in the immunogenic composition according to the present invention are whole inactivated bacterins, i.e. the *M. hyorhinis* antigen, *M. hyosynoviae* antigen and/or the *M. hyopneumoniae* antigens is/are whole inactivated bacterins. Such whole inactivated bacterins can be obtained by the inactivation methods as described herein. Preferably, such whole inactivated bacterins is/are formalin inactivated bacterins.

Preferably such administration results in lessening of the incidence of the particular *mycoplasma* infection in a herd or in the reduction in the severity of clinical signs caused by or associated with the particular *mycoplasma* infection.

According to a further aspect, the immunization of a subject in need with the immunogenic compositions as provided herewith, results in preventing infection of a subject by *mycoplasma* infection. Even more preferably, immunization results in an effective, long-lasting, immunological-response against *mycoplasma* infection. It will be understood that the said period of time will last more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a herd are effectively immunized.

Preferably, a herd of subjects is envisaged in this context which normally, i.e. without immunization, would develop clinical signs normally caused by or associated with a *mycoplasma* infection. Whether the subjects of a herd are effectively immunized can be determined without undue burden by the person skilled in the art. Preferably, the immunization shall be effective if clinical signs in at least 33%, at least 50%, at least 60%, at least 70%, at least 80%, or at least 90% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to subjects that are either not immunized or immunized with an immunogenic composition that was available prior to the present invention but subsequently infected by the particular *mycoplasma* bacteria.

In one aspect of the present invention the subject is selected from a list consisting of swine, cattle, cat, and dog. Thus, according to one aspect a method for immunizing a subject is provided, comprising administering to a subject an immunogenic composition according to the invention, wherein the subject is selected from a list consisting of swine, cattle, cat, and dog.

In one aspect of the present invention the immunogenic composition is administered once. Thus, according to a further aspect a method for immunizing a subject is provided, comprising administering to a subject an immunogenic composition according to the invention, wherein the immunogenic composition is effective in lessening of the incidence of the particular *mycoplasma* infection in a herd or reducing the severity of clinical signs caused by or associated with the particular *mycoplasma* infection after the administration of a single-dose of such immunogenic composition to such subject. It is understood, that such single-dose is administered only once. As shown in Examples 2 and 3 the immunogenic composition as provided herein has been proven to be efficacious after the administration of a single dose to a subject of need.

Thus, when such method comprises the administration of one or more antigens of *M. hyorhinis*, such immunogenic composition is effective in lessening of the incidence of the *M. hyorhinis* infection in a herd or in reducing the severity of clinical signs caused by or associated with the *M. hyorhinis* infection. When such method comprises the administration of one or more antigens of *M. hyopneumoniae*, it is, according to a further aspect, effective in lessening of the incidence of the *M. hyopneumoniae* infection in a herd or in reducing the severity of clinical signs caused by or associated with the *M. hyopneumoniae* infection. Again, the one or more of the *mycoplasma* antigens to be administered by the method of this invention can be whole inactivated bacterins of such *mycoplasma* species as described hereinabove.

Preferably, the single-dose has a total volume between about 0.5 ml and 2.5 ml, more preferably between about 0.6 ml and 2.0 ml, even more preferably between about 0.7 ml and 1.75 ml, still more preferably between about 0.8 ml and 1.5 ml, even more preferably between about 0.9 ml and 1.25 ml, with a single 1.0 ml dose being the most preferred.

However, the immunogenic composition can be administered twice or several times, with a first dose being administered prior to the administration of a second (booster) dose. Preferably, the second dose is administered at least 15 days after the first dose. More preferably, the second dose is administered between 15 and 40 days after the first dose. Even more preferably, the second dose is administered at least 17 days after the first dose. Still more preferably, the second dose is administered between 17 and 30 days after the first dose. Even more preferably, the second dose is administered at least 19 days after the first dose. Still more preferably, the second dose is administered between 19 and 25 days after the first dose. Most preferably the second dose is administered at least 21 days after the first dose. In a preferred aspect of the two-time administration regimen, both the first and second doses of the immunogenic composition are administered in the same amount. Preferably, each dose is in the preferred amounts specified above, with a dose of 1 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition can be administered by other routes as well.

Typically, when a bacterial antigen such *mycoplasma* bacterin is used the immunogenic composition contains an amount of about $10^3$ to about $10^{10}$ colony forming units (CFU) of the bacterial antigen per dose, preferably, about $10^4$ to about $10^9$ CFU of the bacterial antigen per dose, more preferably about $10^5$ to about $10^6$ CFU of the bacterial antigen per dose. If inactivated bacterin is used in the immunogenic composition, the CFU values refer to the amount of *mycoplasma* bacteria prior to inactivation.

For example, the immunogenic composition of the present invention comprising antigens of *M. hyopneumoniae* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose. The immunogenic composition of the present invention comprising antigens of *M. hyorhinis* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose. The immunogenic composition of the present invention comprising antigens of *M. hyosynoviae* are preferably used in amounts of about $10^2$ to about $10^{10}$ CFU per dose, preferably about $10^3$ to about $10^9$ CFU per dose, even more preferably in an amount of about $10^4$ to about $10^8$ CFU per dose, most preferably in an amount of about $10^5$ to about $10^7$ CFU per dose.

Thus, according to a further aspect a method for immunizing a subject is provided, comprising administering to a subject an immunogenic composition according to the invention, wherein the immunogenic composition is effective in lessening of the incidence of the particular *mycoplasma* infection in a herd or in reduction in the severity of clinical signs caused by or associated with the particular *mycoplasma* infection after the administration of a single-dose of such immunogenic composition to such subject, wherein such single-dose comprises $10^2$ to about $10^{10}$ CFU per *mycoplasma* bacteria per dose.

In one aspect of the present invention the method for immunizing a subject in need results in an improvement in an efficacy parameter selected from the group consisting of shorter duration of bacteremia, a lower bacterial load, or combinations thereof, in comparison to a subject of a non-immunized control group of the same species.

The term "shorter duration of bacteremia" means, that the duration of bacteremia in a subject that is immunized with a immunogenic composition is shortened by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 100% in comparison to subjects that are either not immunized or immunized with an immunogenic composition that was available prior to the present invention but subsequently infected by the particular *mycoplasma* bacteria. It is understood, that the duration of bacteremia is determined in a representative number of subjects in each groups (non-immunized and immunized group) prior to its comparison.

The term "lower bacterial load" means, that the bacterial load with wild-type *mycoplasma* bacteria in a subject that is infected with such wild-type *mycoplasma* bacteria is reduced in subjects by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 100% after immunization with a immunogenic composition according to this invention in comparison to subjects that are either not immunized or immunized with an immunogenic composition that was available prior to the present invention but subsequently infected by the particular *mycoplasma* bacteria. It is understood, that the "bacterial load" is determined in a representative number of subjects in each groups (non-immunized and immunized group) prior to its comparison.

Thus, according to a further aspect a method for immunizing a subject is provided, comprising administering to a subject an immunogenic composition according to the invention immunizing a subject in need results in an improvement in an efficacy parameter selected from the group consisting of shorter duration of bacteremia, a lower bacterial load, or combinations thereof, in comparison to a subject of a non-immunized control group of the same species.

In one aspect of the present invention the method is suitable for a subject of about three weeks of age. Thus, according to one aspect, the present application provides a method for immunizing a subject, comprising administering to a subject an immunogenic composition according to the invention, wherein the method is suitable for a subject of about three weeks of age.

Advantageously, the experimental data provided by the present invention disclose effectiveness of the immunogenic composition in piglets of about 3 weeks of age.

Preferably, said subject to be immunized is between 1 day of age to 21 days of age, more preferably, said subject to be immunized is between 1 day of age to 10 days of age, even more preferably, between 1 day of age to 9 days of age, even more preferably between 1 day of age to 8 days of age, even more preferably between 1 day of age to 7 days of age, even more preferably between 1 day of age to 6 days of age, even more preferably between 1 day of age to 5 days of age, even more preferably between 1 day of age to 4 days of age, even more preferably between 1 day of age to 3 days of age, even more preferably 1 or 2 day(s) of age, and most preferably 1 day of age.

Thus, according to one aspect, a method for immunizing a subject is provided, comprising administering to a subject an immunogenic composition according to the invention immunizing a subject in need, wherein said subject to be immunized is between 1 day of age to 21 days of age.

The present invention also relates to any of the immunogenic composition provided herewith in the use of any of the methods as described herein, e.g. in the use for the treatment and/or prophylaxis of *mycoplasma* infections in a subject, or in the use of the immunization of a subject against such *mycoplasma* infection.

Such immunogenic composition comprises a) one or more antigens of *M. hyosynoviae* and one or more antigens selected from the group consisting of *M. hyopneumoniae, M. hyorhinis* and the combination thereof; and b) a pharmaceutically acceptable carrier.

According to a further aspect, the immunogenic composition according to the invention comprises: a) one or more antigens of *M. hyorhinis* and one or more antigens of *M. hyosynoviae*; and b) a pharmaceutically acceptable carrier. According to a further aspect, the immunogenic composition also comprises one or more antigens of *M. hyopneumoniae*.

If the immunogenic composition is produced in a serum-reduced, eukaryotic cell system as described herein, than the immunogenic composition can in general comprise one or more antigens of a *mycoplasma* bacterium selected from the group consisting of *M. hyorhinis*, *M. hyopneumoniae*, *M. hyosynoviae* and any combination thereof as further defined herein. According to a further aspect defined hereinabove, such immunogenic composition can comprise one or more components of a eukaryotic cell system in addition to the one or more antigens of a *mycoplasma* bacterium selected from the group consisting of *M. hyorhinis*, *M. hyopneumoniae*, *M. hyosynoviae*, and any combination thereof.

According to a further aspect the one or more of the *mycoplasma* antigens used for immunizing the subject in need is/are whole inactivated bacterin. This aspect of the present invention encompasses that either one of the *mycoplasma* antigens is a whole inactivated bacterin. However, this aspect of the present invention also encompasses that all antigens in the immunogenic composition according to the present invention are whole inactivated bacterins, i.e. the *M. hyorhinis* antigen, *M. hyosynoviae* antigen and/or the *M. hyopneumoniae* antigens is/are whole inactivated bacterins. Such whole inactivated bacterins can be obtained by the inactivation methods as described herein. Preferably, such whole inactivated bacterins is/are formalin inactivated bacterins.

Preferably such use results in lessening of the incidence of the particular *mycoplasma* infection in a herd or in the reduction in the severity of clinical signs caused by or associated with the particular *mycoplasma* infection.

The present invention also relates to the use of the immunogenic composition as described herein for the treatment and/or prophylaxis of *mycoplasma* infections in a subject or for the immunization of a subject against a *mycoplasma* infection.

Such immunogenic composition comprises a) one or more antigens of *M. hyosynoviae* and one or more antigens selected from the group consisting of *M. hyopneumoniae*, *M. hyorhinis* and the combination thereof; and b) a pharmaceutically acceptable carrier.

According to a further aspect, the immunogenic composition according to the invention comprises: a) one or more antigens of *M. hyorhinis* and one or more antigens of *M. hyosynoviae*; and b) a pharmaceutically acceptable carrier. According to a further aspect, the immunogenic composition also comprises one or more antigens of *M. hyopneumoniae*.

If the immunogenic composition is produced in a serum-reduced, eukaryotic cell system as described herein, then the immunogenic composition can in general comprise one or more antigens of a *mycoplasma* bacterium selected from the group consisting of *M. hyorhinis*, *M. hyopneumoniae*, *M. hyosynoviae* and any combination thereof as further defined herein. According to a further aspect defined hereinabove, such immunogenic composition can comprise one or more components of a eukaryotic cell system in addition to the one or more antigens of a *mycoplasma* bacterium selected from the group consisting of *M. hyorhinis*, *M. hyopneumoniae*, *M. hyosynoviae* and any combination thereof.

According to a further aspect the one or more of the *mycoplasma* antigens used for immunizing the subject in need is/are whole inactivated bacterin. This aspect of the present invention encompasses that either one of the *mycoplasma* antigens is a whole inactivated bacterin. However, this aspect of the present invention also encompasses that all antigens in the immunogenic composition according to the present invention are whole inactivated bacterins, i.e. the *M. hyorhinis* antigen, *M. hyosynoviae* antigen and/or the *M. hyopneumoniae* antigens is/are whole inactivated bacterins. Such whole inactivated bacterins can be obtained by the inactivation methods as described herein. Preferably, such whole inactivated bacterins is/are formalin inactivated bacterins.

Preferably such use results in lessening of the incidence of the particular *mycoplasma* infection in a herd or reduction in the severity of clinical signs caused by or associated with the particular *mycoplasma* infection.

EXAMPLES

The following examples are only intended to illustrate the present invention. They shall not limit the scope of the claims in any way.

Example 1

Cultivation of *Mycoplasma* Bacteria in MDCK Cells or McCoy Cell, Respectively

A. Cultivation of *M. hyorhinis*, *M. hyosynoviae* and *M. hyopneumoniae* in MDCK cells

*M. hyorhinis*:

Confluent T75 flask(s) of MDCK cells are trypsinized and subcultured into 5, T150 flasks (1:10 split) using MEM+5% FBS. Flasks are incubated at 37° C.+5% $CO_2$ until an approximately 95-100% confluent monolayer is observed. Media is decanted and flasks rinsed twice with 1×PBS. Four to five mls of *M. hyorhinis* is added to each flask (MOI=10-100). Confluent cells in flasks are infected under the same incubation conditions as above for no less than 2 hours. After the infection period, sufficient Infection Media (MEM+2% FBS), pre-warmed to approximately 37° C., is added to each flask for a total volume of 60 ml per flask. Flasks are incubated until >90% CPE was noted (approximately 3-7 days). Cell suspensions are collected from each flask and pooled together (Passage=n). The pooled material is used to infect new flasks of approximately 95-100% confluent MDCK cells in the same manner as previous infection (Passage=n+1), increasing the number of flasks used to achieve a sufficient final volume as deemed necessary (Passage=n+2, Passage=n+3, etc).

*M. hyosynoviae:*

*M. hyosynoviae* is cultured in the same manner as *M. hyorhinis* with a few modifications: Infection Media contains DMEM+2% FBS+1% arginine solution; *M. hyosynoviae* has typically not exhibited CPE so color change and turbidity of the media is the key indicator to subculture to the next passage.

*M. hyopneumoniae:*

*M. hyopneumoniae* is cultured in the same manner as *M. hyorhinis*. Depending on the strain used for infection, CPE may or may not be present. Therefore, color change and turbidity of media can be used as the indicator to subculture to the next passage.

B. Cultivation Conditions for, *M. hyorhinis*, *M. hyosynoviae* and *M. hyopneumoniae* in McCoy Cells

*M. hyorhinis:*

McCoy cells are grown as suspension cultures in stir flasks in modified EMEM supplemented with 10% FBS. Cells are subcultured by seeding new flasks so as to have a final concentration of $10^5$-$10^6$ cells/ml. For *M. hyorhinis*, a 500 ml cell suspension at a concentration of $10^5$-$10^6$ cells/ml in a 3 L flask is seeded with 1 ml $10^7$-$10^8$ CFUs. Flasks are incubated at 37° C. in the presence of 5% $CO_2$ on a magnetic stir plate for 3-7 days. *Mycoplasma* growth is ascertained by visible acidic pH change and increase in turbidity. *Mycoplasma* growth is also evaluated by PFU assays to determine counts.

*M. hyosynoviae:*

*M. hyosynoviae* is cultivated in a similar manner as *M. hyorhinis*. A 500 ml cell suspension at a concentration of $10^5$-$10^6$ cells/ml in a 3 L flask is seeded with 1 ml $10^5$-$10^7$ CFUs. Flasks are incubated at 37° C. in the presence of 5% $CO_2$ on a magnetic stir plate for approximately 2 weeks. Both pH change and increase in turbidity are used to determine growth in addition PFU assays to determine counts.

*M. hyopneumoniae:*

*M. hyopneumoniae* is cultivated in a similar manner as *M. hyorhinis* and *M. hyosynoviae*. A 500 ml cell suspension at a concentration of $10^5$-$10^6$ cells/ml in a 3 L flask is seeded with 1 ml $10^5$-$10^7$ CFUs. Flasks are incubated at 37° C. in the presence of 5% $CO_2$ on a magnetic stir plate for around 2 weeks. Both pH change and increase in turbidity can be used to determine growth in addition PFU assays to determine counts.

C. Cultivation of *Mycoplasma* Species with Various Serum Types

To evaluate whether a *mycoplasma* species can be cultivated in serum from different species, MDCK cells are infected with *M. hyorhinis* and cultured in Fetal Bovine Serum, Porcine Serum, Rabbit Serum, Chicken Serum or Horse Serum. For each serum type, the cultivation of *M. hyorhinis* in MDCK cells is performed as described above (i.e., 5% serum for cell growth and 2% serum for infection). *M. hyorhinis* is harvested at four days post-infection per standard method. A CCU (color changing unit) assay is performed to determine the live titer of *M. hyorhinis*. Further, a qPCR (quantitative real time Polymerase chain reaction) is performed to determine the total genomic content of *M. hyorhinis*. An exemplary experiment is shown in Table 1.

TABLE 1

Cultivation of *M. hyorhinis* with various serum types

| Serum type | qPCR log (gc/μl) | CCU50 (log/ml) |
|---|---|---|
| Fetal Bovine Serum | 6.15 | 8.00 |
| Porcine Serum | 6.06 | 8.50 |
| Rabbit Serum | 6.11 | 8.33 |
| Chicken Serum | 6.31 | 8.00 |
| Horse Serum | 6.49 | 9.00 |

Table 1 shows that the titers measured either by CCU assay or qPCR are similar for the various serum types. Further, western blot data (not shown) support this data. Thus, *M. hyorhinis* could be cultivated in MDCK cells irrespective of which serum type was used for cultivation.

Example 2

Preparation of Vaccines

When final passage is ready to harvest (>90% CPE present), a single freeze-thaw cycle is performed on all flasks by placing them into a <−60° C. freezer for >2 hours, quickly thawing at 37° C., collecting and pooling lysate, and pipetting up and down several times to homogenize. Generally, 10-20% glycerol is added to the suspension and homogenized. This suspension is aliquoted into working volumes. Stocks kept at <−60° C. until needed.

Appropriate volumes of the above stocks are inactivated with 0.2% formalin. Excess formalin is neutralized with sodium bisulfite at the time of vaccine blending. Vaccines are blended with Montanide™ ISA 207 VG adjuvant or with CARBOPOL® adjuvant. Vaccines are stored at 2-7° C.

Example 3

Assessment of Effectiveness of the Vaccines

The efficacy of vaccines is evaluated based on the ability to induce an antibody response (as well as the titer by ELISA) after administration in swine.

Animal Care

Animals are in good health and nutritional status before a study is initiated. Prior to the randomization procedure and record a health examination is conducted. Non-medicated feed is used throughout the duration of the study. Feed rations are appropriate for the age, condition, and species of test animal according to facility standard operating procedure. Water is provided ad libitum throughout the study.

Assessment of Effectiveness of *M. hyorhinis* and *M. hyopneumoniae* Vaccines after Administration in Swine.

*M. hyorhinis:*

On D0 and again on D21, conventional piglets of 6 weeks ±5 days of age are administered a 2 ml dose (7.1-7.3 log 10 CCU/dose) of *M. hyorhinis* vaccine intramuscularly. *M. hyorhinis* is prepared as above; i.e. cultured in MDCK cells as described above. The vaccine is adjuvanted with Montanide ISA207VG or CARBOPOL®. PBS is used as Placebo. The pigs are observed daily for general health. Blood is collected prior to vaccination at D0, 7, 14, 21, 28, 35 and 42. The serum is tested for *M. hyorhinis* specific antibodies by BIVI R&D Indirect ELISA. For the BIVI R&D ELISA, an S/P ratio of >0.200 is considered positive.

In the example shown in Table 2, the *M. hyorhinis* ELISA indicates a strong antibody response. Six/six (6/6) (100%) animals vaccinated with *M. hyorhinis*-MDCK+Montanide ISA207VG were positive two weeks after the first dose (D14). All animals remained positive through D42, with a boost in titers noted one week after the second dose (D28). Animals vaccinated with *M. hyorhinis*-MDCK+CARBOPOL® also show an antibody response.

TABLE 2

*M. hyorhinis* ELISA results

| | Pre | D0 | D7 | D14 | D21 | D28 | D35 | D42 |
|---|---|---|---|---|---|---|---|---|
| *M. hyorhinis* MDCK + Montanide ISA207VG | 0.00 | 0.003 | 0.043 | 0.972 | 1.123 | 1.340 | 1.152 | 1.133 |
| *M. hyorhinis* MDCK + CARBOPOL ® | 0.002 | 0.018 | 0.059 | 0.095 | 0.122 | 0.354 | 0.375 | 0.409 |
| Placebo (PBS) | 0.001 | 0.005 | 0.011 | 0.015 | 0.021 | 0.031 | 0.057 | 0.070 |

Similar antibody response results post-vaccination were achieved using *M. hyorhinis* cultured in McCoy cells (data not shown). Further, similar results for an antibody response post-vaccination were achieved in piglet of 3 weeks ±5 days of age (data not shown). Similar results were obtained after a single dose administration (data not shown).

M. hyopneumoniae:

On D0 and again on D21, conventional piglets of 6 weeks ±5 days of age were administered a 2 ml dose (8.0-8.5 log 10 CCU/dose) of M. hyopneumoniae vaccine intramuscularly. The vaccine is adjuvanted with Montanide ISA207VG. PBS is used as Placebo. The pigs are observed daily for general health. Blood is collected prior to vaccination at D0, 7, 14, 21, 28, 35 and 42 to test for the presence of M. hyopneumoniae antibodies. In the example shown in Table 3, a commercial IDEXX ELISA was used. For the IDEXX ELISA, an S/P ratio of >0.400 is considered positive.

In the example shown in Table 3, the M. hyopneumoniae ELISA indicated a strong antibody response. For the M. hyopneumoniae MDCK+ISA207 vaccinated animals, 3/6 (50%) animals were positive on D14 and 5/6 (83.3%) on D21 with 6/6 (100%) positive on D28, 35, and 42.

TABLE 3

M. hyopneumoniae IDEXX ELISA results

| | Pre | D0 | D7 | D14 | D21 | D28 | D35 | D42 |
|---|---|---|---|---|---|---|---|---|
| M. hyopneumoniae MDCK + Montanide ISA207VG | −0.024 | −0.022 | 0.034 | 0.601 | 0.949 | 1.775 | 1.986 | 1.895 |
| Placebo (PBS) | −0.019 | 0.011 | −0.021 | −0.015 | −0.025 | −0.025 | 0.016 | 0.016 |

Similar results were obtained after a single dose administration, data not shown.

Example 4

Effectiveness of Vaccines Obtained from Mycoplasma Bacteria Cultured in an Eukaryotic Cell Line Versus Vaccines Obtained from Mycoplasma Bacteria Cultured in a Cell Free System Fifty-four CD/CD animals at 8 weeks ±5 days of age are divided into six groups. Group V1 and V2 each receive an inactivated isolate of M. hyorhinis cultured in MDCK cells and CM (complex medium; such as proteose peptone based medium containing porcine serum and yeast extract or Friis-based media), respectively; Group V3 and V4 received an inactivated isolate of M. hyorhinis cultured in MDCK cells and CM, respectively. All vaccines are adjuvanted with Montanide ISA207VG; dosage and route were 2×2 ml doses by intramuscular injection with one dose given on D0 and the second on D21. Group CC (control group) received an antigen-free placebo (PBS) in the same fashion. Group SC (strict control) received no treatment throughout the study, serving as strict control animals. On D42, 43, and 44, pigs in Group V1-V4 and CC are challenged with a virulent M. hyorhinis. Dosage and route of administration is 40 ml intraperitoneal, 15 ml intravenous, and 15 ml intranasal, respectively. Blood is collected weekly from D0 through the end of the study (D58) for M. hyorhinis-specific ELISA testing. For the R&D M. hyorhinis ELISA, an S/P ratio of >0.200 was considered positive. In the exemplary study shown in Table 4, all pigs in Group SC remained negative throughout the study, indicating a lack of exposure to M. hyorhinis. Groups V I-V4 and CC were negative on D0 and 7. However, serology results varied between the CM-based and MDCK-based vaccines. When compared to the CM-based vaccines, the MDCK-based vaccines showed earlier on-set of sero-conversion, greater numbers of sero-positive pigs, and higher serological titers.

TABLE 4

M. hyorhinis ELISA results
M. hyorhinis ELISA Average S/P Ratios by Group

| Group | D0 | D7 | D14 | D21 | D28 | D35 | D42 | D49 | D58 |
|---|---|---|---|---|---|---|---|---|---|
| MHRN001 − MDCK | −0.002 | 0.010 | 0.199 | 0.482 | 0.916 | 0.971 | 0.929 | 1.056 | 0.991 |

TABLE 4-continued

M. hyorhinis ELISA results
M. hyorhinis ELISA Average S/P Ratios by Group

| Group | D0 | D7 | D14 | D21 | D28 | D35 | D42 | D49 | D58 |
|---|---|---|---|---|---|---|---|---|---|
| MHRN001 – CM (V2) | 0.001 | 0.009 | 0.031 | 0.081 | 0.395 | 0.401 | 0.370 | 0.793 | 0.770 |
| MHRN002 – MDCK | 0.004 | 0.014 | 0.157 | 0.424 | 0.981 | 1.023 | 0.953 | 1.097 | 1.086 |
| MHRN002 – CM (V4) | 0.003 | 0.011 | 0.017 | 0.047 | 0.298 | 0.299 | 0.263 | 0.704 | 0.608 |
| Placebo (CC) | 0.004 | 0.004 | 0.009 | 0.023 | 0.021 | 0.029 | 0.031 | 0.262 | 0.433 |
| Strict Control (SC) | −0.003 | −0.002 | −0.003 | 0.005 | 0.008 | 0.015 | 0.021 | 0.031 | 0.060 |

Titration experiments are performed to compare cell culture-based vaccines to vaccines from *mycoplasma* bacteria cultured in a cell free system.

*M. hyorhinis* is cultured in McCoy cells as described above or cultured in CM (complex medium), respectively.

Vaccines are made with McCoy antigen using undiluted antigen ("McCoy+ISA full"), 1:10 antigen ("McCoy+ISA 1:10"), and 1:100 antigen ("McCoy+ISA 1:100") all blended 1:1 with Montanide ISA207VG as adjuvants. Vaccines using CM derived antigen are made in the same manner.

Pigs (three weeks of age at the time of vaccination) are vaccinated with a single 2 mL dose administered IM on Day 0.

As shown in Table 5, group averages from the exemplary study were all "negative" prior to challenge (D0-D21), though, the "McCoy+ISA full" and "McCoy+ISA 1:10" showed responses trending towards positive. At one week post-challenge (D28), all vaccinate groups responded with the exception of "CM+ISA 1:100".

From Table 5 it is apparent that each antigen type (McCoy, CM) exhibits a standard titration effect (Full>1:10>1:100). Further, from Table 5 it is apparent that the "McCoy+ISA full" and "McCoy+ISA 1:10" vaccinates have higher average scores than the "CM+ISA full" antigen, and that holds true through termination at D42. Groups with positive (S/P≥0.200) averages post-challenge are the "McCoy+ISA full" and "McCoy+ISA 1:10" groups. The McCoy Full vaccine and 1:10 dilution showed a higher sero-response than CM Full vaccine both pre-challenge and post-challenge. Furthermore, animals vaccinated with McCoy 1:100 also demonstrated a response distinguishable from placebo (non-vaccinates) and CM 1:100 groups (CM 1:100 response, or lack thereof, was equivalent to non-vaccinates). The titration experiments demonstrated that cell culture-based vaccines had better serological results compared to vaccines from *mycoplasma* bacteria cultured in a cell free system.

TABLE 5

M. hyorhinis ELISA results
M. hyorhinis ELISA Average S/P Ratios by Group

| Group | D0 | D7 | D14 | D21 | D28 | D35 | D42 |
|---|---|---|---|---|---|---|---|
| McCoy + ISA full | 0.002 | 0.012 | 0.032 | 0.117 | 0.312 | 0.298 | 0.325 |
| McCoy + ISA 1:10 | 0.000 | 0.005 | 0.065 | 0.107 | 0.291 | 0.193 | 0.221 |
| McCoy + ISA 1:100 | 0.001 | 0.001 | −0.001 | 0.000 | 0.145 | 0.118 | 0.150 |
| CM + ISA full | 0.002 | 0.009 | 0.011 | 0.034 | 0.190 | 0.163 | 0.190 |
| CM + ISA 1:10 | −0.001 | 0.017 | 0.003 | 0.014 | 0.114 | 0.132 | 0.176 |
| CM + ISA 1:100 | −0.002 | 0.000 | −0.002 | 0.001 | 0.019 | 0.043 | 0.093 |
| Placebo: PBS + ISA | −0.001 | 0.002 | −0.002 | −0.002 | 0.021 | 0.039 | 0.081 |
| Strict Control | −0.002 | −0.001 | −0.002 | −0.002 | −0.002 | 0.008 | 0.024 |

Example 5

Effectiveness of the Multivalent Vaccine Comprising Antigen of *M. hyosynoviae*, *M. hyopneumoniae* and *M. hyorhinis*

In this study, 15 CD/CD animals at 11 weeks ±5 days of age were administered a single 2 mL dose, IM, of a tri-valent prototype *Mycoplasma* combination vaccine. The vaccine consisted of inactivated *M. hyorhinis*, inactivated *M. hyopneumoniae*, and inactivated *M. hyosynoviae*. All *mycoplasma* species were prepared in MDCK cells. The vaccine was adjuvanted with Montanide ISA207VG. Blood samples were collected weekly from Day 0 through Day 28. Antibody levels in serum were monitored by *M. hyorhinis* BIVI R&D ELISA and *M. hyopneumoniae* IDEXX ELISA. No serological assay for *M. hyosynoviae* was available at the time of this study.

The *M. hyorhinis* ELISA indicated a strong antibody response two weeks post-vaccination (D14), with 11/15 (73.3%) of the pigs positive and 15/15 (100%) positive by D21.

The *M. hyopneumoniae* IDEXX ELISA results indicated that four pigs were positive (S/P>0.400) for *M. hyopneumoniae* antibodies on D0. If these four pigs are excluded, five different pigs seroconverted to *M. hyopneumoniae* by D28. Three of these five pigs were positive on D21.

TABLE 6

M. hyorhinis ELISA results
M. hyorhinis ELISA Group Average S/P Ratio

| D0 | D7 | D14 | D21 | D28 |
|---|---|---|---|---|
| 0.043 | 0.050 | 0.406 | 0.873 | 0.866 |

TABLE 7

| M. hyopneumoniae IDEXX ELISA results M. Hyopneumoniae IDEXX ELISA Group Average S/P Ratio | | | | |
|---|---|---|---|---|
| D0 | D7 | D14 | D21 | D28 |
| 0.294 | 0.255 | 0.259 | 0.287 | 0.421 |

Results for *M. hyorhinis* indicated a lack of interference by the remaining fractions in the vaccine. Moreover, *M. hyorhinis* antigen levels blended in the combination vaccine as used in this study are sufficient to induce a measurable antibody response after a single 2 mL dose. *M. hyopneumoniae* results demonstrated some sero-conversion. Higher blending levels for this fraction can be beneficial for increasing sero conversion. Results from the *M. hyorhinis* and *M. hyopneumoniae* fractions indicated a lack of interference by these species.

The invention claimed is:

1. An immunogenic composition comprising: a) a bacterin comprising one or more antigens of *M. hyorhinis* and a bacterin comprising one or more antigens of *M. hyosynoviae* wherein at least one bacterin of *M. hyorhinis* and *M. hyosynoviae* bacteria is co-cultivated in a eukaryotic cell system comprising MDCK cells or McCoy cells grown in swine serum free medium; b) one or more components of the MDCK cells or McCoy cells harvested from the *M. hyorhinis* and/or *M. hyosynoviae* bacteria co-culture of a); and c) a pharmaceutically acceptable carrier.

2. The immunogenic composition of claim 1, wherein said immunogenic composition further comprises a bacterin comprising one or more antigens of *M. hyopneumoniae*.

3. The immunogenic composition of claim 1, wherein said bacterins are formalin or binary ethylenimine (BEI) inactivated bacterins.

4. The immunogenic composition of claim 1, obtained by a method comprising the steps of a) co-cultivating a *mycoplasma* bacteria selected from the group consisting of *M. hyorhinis*, *M. hyopneumoniae*, *M. hyosynoviae*, and any combinations thereof, in a swine serum free and a serum-reduced, eukaryotic cell system comprising MDCK cells or McCoy cells; b) obtaining such *mycoplasma* cultivated bacteria as a bacterin comprising *mycoplasma* antigens; c) obtaining one or more components of the MDCK cells or McCoy cells harvested from the *M. hyorhinis* and/or *M. hyosynoviae* bacteria co-culture of b); and d) adding pharmaceutically acceptable carrier.

5. The immunogenic composition of claim 4, wherein the bacterin comprises *mycoplasma* antigens of *M. hyorhinis*.

6. The immunogenic composition of claim 4, wherein the bacterin comprises *mycoplasma* antigens of *M. hyopneumoniae*.

7. The immunogenic composition of claim 6, wherein the bacterin comprises a combination of *mycoplasma* antigens of *M. hyorhinis* and *M. hyopneumoniae* or antigens of *M. hyorhinis* and *M. hyopneumoniae* and *M. hyosynoviae*.

8. The immunogenic composition of claim 4, wherein said immunogenic composition has an increased immunogenicity compared to an immunogenic composition comprising the same *mycoplasma* antigen obtained from *mycoplasma* cultivated in a cell free culturing system.

9. The immunogenic composition of claim 1, wherein said components of the eukaryotic cells are attached to *mycoplasma* antigens in the bacterin.

10. The immunogenic composition of claim 4, wherein the whole inactivated bacterins are formalin or binary ethylenimine (BEI) inactivated bacterins.

11. An immunogenic composition that comprises a) one or more *mycoplasma* antigens of *mycoplasma* bacteria selected from the group consisting of *M. hyorhinis*, *M. hyopneumoniae*, *M. hyosynoviae* and any combination thereof; and b) one or more components of primary eukaryotic cells and/or eukaryotic cells derived from plants or animals which have been co-cultured with at least one of the *mycoplasma* bacteria selected from the group consisting of *M. hyorhinis*, *M. hyopneumoniae*, *M. hyosynoviae* and any combination thereof of a).

12. The immunogenic composition of claim 11, wherein the *mycoplasma* antigen are antigens of *M. hyorhinis*.

13. The immunogenic composition of claim 11, wherein the *mycoplasma* antigen are antigens of *M. hyopneumoniae*.

14. The immunogenic composition of claim 11, wherein the *mycoplasma* antigen are antigens of *M. hyorhinis* and *M. hyopneumoniae* or antigens of *M. hyorhinis* and *M. hyopneumoniae* and *M. hyosynoviae*.

15. The immunogenic composition of claim 11, wherein said eukaryotic cell system comprises MDCK cells or McCoy cells or one or more components thereof.

16. The immunogenic composition of claim 11, wherein components of a eukaryotic cell system include serum.

17. The immunogenic composition of claim 11, wherein the immunogenic composition is free of swine serum.

18. The immunogenic composition of claim 11, wherein said components of the eukaryotic cells are attached to the *mycoplasma* antigen.

19. The immunogenic composition of claim 11, wherein one or more of the antigens are whole inactivated bacterins.

20. The immunogenic composition of claim 19, wherein the whole inactivated bacterins are formalin inactivated bacterins.

21. The immunogenic composition of claim 11, wherein said immunogenic composition has an increased immunogenicity compared to an immunogenic composition comprising the same *mycoplasma* antigen obtained from *mycoplasma* cultivated in a cell free culturing system.

22. The immunogenic composition of claim 1, wherein said composition is administered to a subject selected from the list consisting of swine, cattle, cat and dog.

23. The immunogenic composition of claim 2, wherein said composition is administered to a subject selected from the list consisting of swine, cattle, cat and dog.

24. The immunogenic composition of claim 21, wherein said composition is administered to a subject selected from the list consisting of swine, cattle, cat and dog.

25. The immunogenic composition of claim 11, wherein said composition is administered to a subject selected from the list consisting of swine, cattle, cat and dog.

26. The immunogenic composition of claim 1, wherein said immunogenic composition is formulated for a single-dose administration.

27. The immunogenic composition of claim 1, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

28. The immunogenic composition of claim 1, wherein said pharmaceutically acceptable carrier is an adjuvant selected from the group consisting of aluminum hydroxide, aluminum phosphate, saponins, water-in-oil emulsion, oil-in-water emulsion, water-in-oil-in-water emulsion, polymers of acrylic or methacrylic acid, copolymers of maleic anhydride and alkenyl derivative, Block co-polymer, monophosphoryl lipid A, Avridine lipid-amine, heat-labile enterotoxin from *E. coli*, cholera toxin, muramyl dipeptide, and combinations thereof.

29. The immunogenic composition of claim 1, wherein said pharmaceutically acceptable carrier is a water-in-oil-in-water emulsion or a carbomer.

\* \* \* \* \*